United States Patent [19]
Shah et al.

[11] Patent Number: 5,645,799
[45] Date of Patent: Jul. 8, 1997

[54] APPARATUS FOR A CONTINUOUS POLYMER DOSAGE OPTIMIZATION AND WASTE WATER ANALYSIS SYSTEM

[75] Inventors: Jitendra T. Shah; Ananthasubramanian Sivakumar, both of Naperville; David W. Scheimann, Joliet, all of Ill.

[73] Assignee: Nalco Chemical Company, Naperville, Ill.

[21] Appl. No.: 552,215

[22] Filed: Nov. 2, 1995

Related U.S. Application Data

[63] Continuation-in-part of Ser. No. 399,255, Mar. 6, 1995, abandoned.

[51] Int. Cl.$^6$ .................................................. G01N 21/64
[52] U.S. Cl. .................... 422/62; 422/3; 422/108; 422/111; 210/709
[58] Field of Search .................... 422/62, 3, 105, 422/107, 108, 111; 210/709, 745, 746

[56] References Cited

U.S. PATENT DOCUMENTS

| | | | |
|---|---|---|---|
| 5,389,548 | 2/1995 | Hoots et al. | 436/6 |
| 5,411,889 | 5/1995 | Hoots et al. | 436/6 |
| 5,413,719 | 5/1995 | Sivakumar et al. | 210/708 |
| 5,435,969 | 7/1995 | Hoots et al. | 436/6 |

*Primary Examiner*—Lyle A. Alexander
*Attorney, Agent, or Firm*—James J. Drake; Robert A. Miller

[57] ABSTRACT

The invention comprises an apparatus for optimizing the dosage of a chemical waste water treatment agent using a fluorescent tracer by processing a sample of the waste water stream and allowing continuous on-stream monitoring of the performance of the chemical waste water treatment agent. The apparatus is comprised of a series of components that sample the waste stream, process the sample for analysis, analyze the sample, record the data in a historical database and, based upon the analysis as compared to historical data, adjust the chemical feed system to optimize the chemical waste water treatment agent according to the programmed optimization logic.

8 Claims, 10 Drawing Sheets

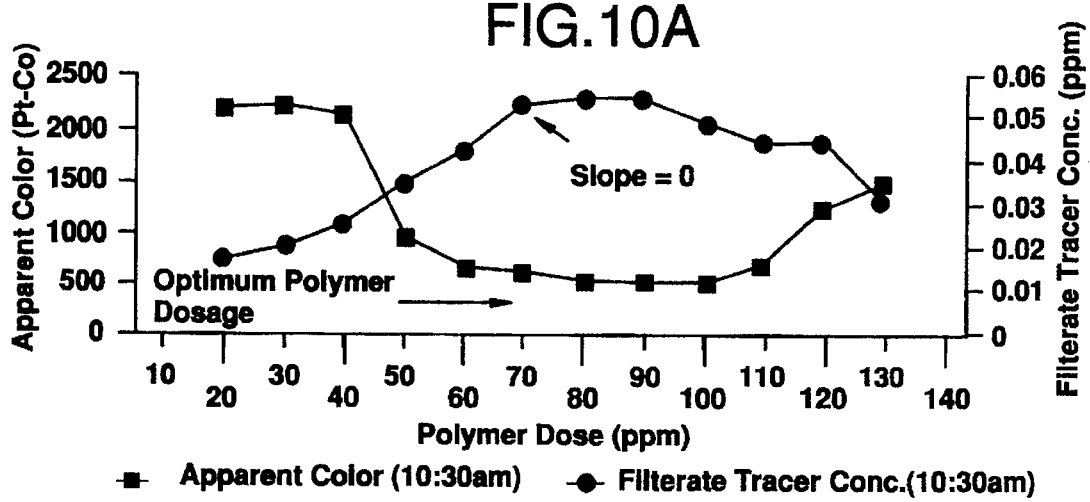
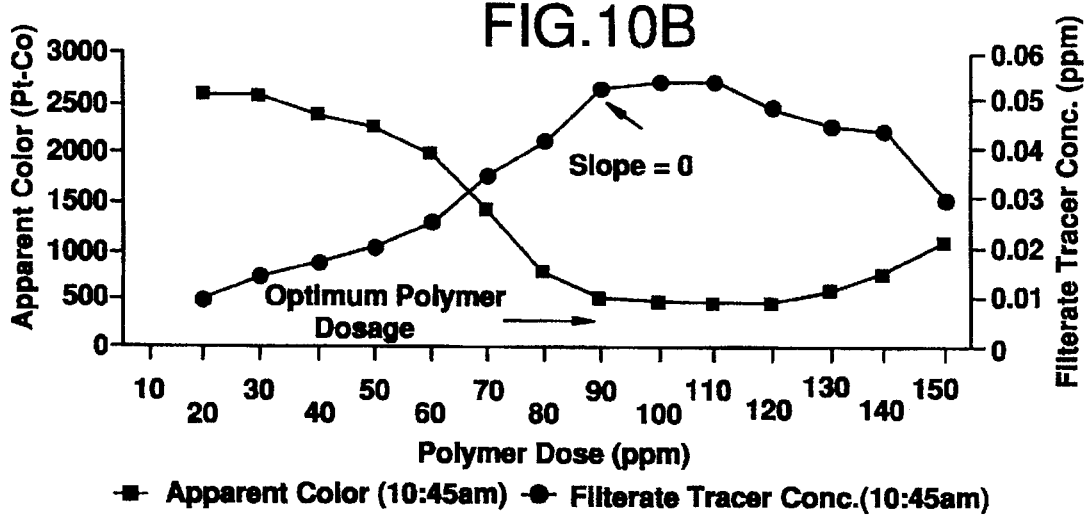
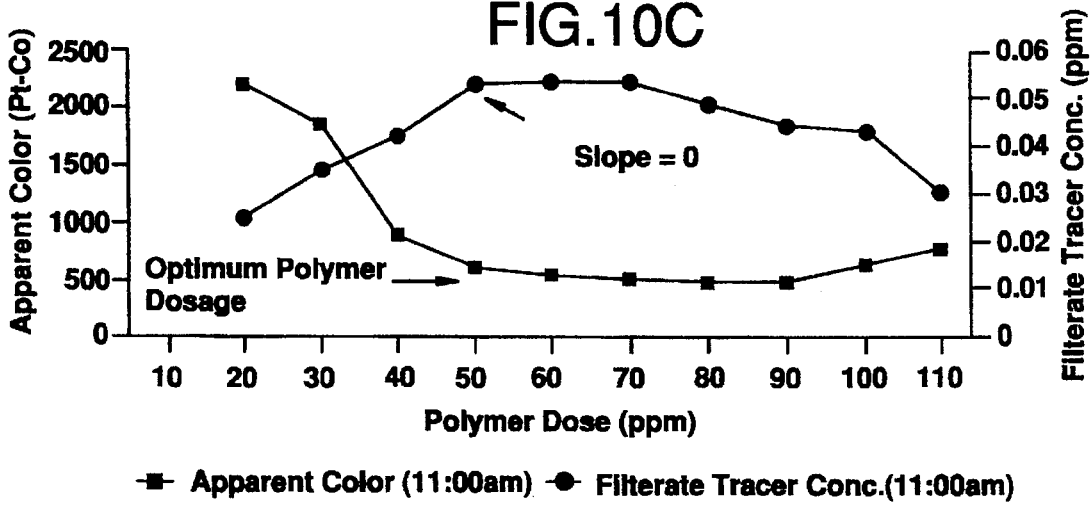

APPARATUS FOR A CONTINUOUS POLYMER DOSAGE OPTIMIZATION AND WASTE WATER ANALYSIS SYSTEM

BACKGROUND OF THE INVENTION

Reference to Related Patent

The present application is a continuation-in-part of application Ser. No. 08/399,255, filed Mar. 6, 1995, now abandoned by Jitendra T. Shah, Ananthasubramanian Sivakumar and David W. Scheimann, entitled "Apparatus for a Continuous Polymer Dosage Optimization and Waste Water Analysis System", the disclosure of which is incorporated herein by reference.

FIELD OF THE INVENTION

This invention relates to a an apparatus for continuous on-stream monitoring and optimization of the performance of a product added to treat a waste water.

DESCRIPTION OF THE PRIOR ART

Industrial waste waters, depending upon the specific type of wastewater, usually require chemical treating agents to remove color, suspended solids, oil or to dewater sludge prior to their discharge into natural waters such as streams, ponds, lakes, etc.. The amount of chemical agent added to the wastewater is critical for optimum performance. Both underdosing and overdosing of the chemical agent result in poor performance and may lead to non-conformance with the discharge limits set by the EPA. Because the wastewater characteristics and chemical treatment agent demand are constantly changing, it is essential to continuously optimize the chemical dosage.

Various approaches have been tried to optimize the chemical feed to wastewater based upon a wide variety of parameters. Unfortunately, these measures have met without much success for a variety of reasons. Most of the approaches were based upon physical parameters such as rheology or light transmission. The problem with this is that these parameters are affected by factors other than the wastewater characteristics, one example of this is shear in the system. As a result, they have not been successful.

The measurement of charge of the waste stream by colloid titration to control the feed is not practical due to interference caused by the presence of other materials present in the waste stream and the methods time consuming nature. The streaming current or the streaming potential in the filtrate shows good correlation with the performance of the chemical treating agent and thus the chemical feed can be optimized using a streaming current detector. (1) S. K. Dental and M. M. Abu-Orf, paper presented at WEF Conference, October, 1994. However, there are two main problems associated with continuous use of this technique:

1. Interference's from other charged species in the waste water stream.

2. Fouling of the monitor from solids, oil ect. present in the waste stream.

Direct measurement of the chemical treating agents concentration in the waste stream would be the best method to control the chemical agent feed rate. However, in most cases this is not possible due to interference's from species present in the waste water. An estimate of the chemical concentration of the chemical treatment agent in the waste water stream can be obtained by using fluorescent tracers. Fluorescence spectroscopy is an extremely rapid and sensitive technique. By properly processing the sample for analysis and choosing an appropriate excitation and emission wavelength, the interference's from the unwanted species can be eliminated.

Typically, industrial wastewater treatment systems are once-through systems and contain both solids(oil) and liquids. In such systems, the fluorescent tracer must meet the following criteria:

1. The tracer should not be inert and interact with the chemical only since the measurement of the tracer concentration in the filtrate would be an indicator of only the theoretical zero-consumption concentration of the chemical and not the actual filtrate concentration of the chemical.

2. The tracer should not interact with the solids or the oil by itself since such a tracer concentration in the filtrate would not be an indicator of the chemical consumption and hence the chemical performance.

Though the fluorescent tracer technique is very sensitive and eliminates interference's from other species in the filtrate, it is still essential to separate the solids/oil from the water prior to the fluorescence analysis of the filtrate. The presence of solids in the filtrate would cause distortion in the fluorometer reading as a result of light scattering and the presence of the treatment chemical containing the fluorescent tracer that has partitioned on the surface of the solids. In order to operate the polymer dosage optimization system on a continuous basis and to analyze only for the portion of the product that has partitioned into the liquid phase, the incorporation of a solid-liquid separation device capable of providing reliable and continuous solids removal is needed.

The three most common types of solid-liquid separation devices used in low volume applications are cyclone separators, centrifuges and filter media based devices. Filter media based devices consist of devices such as cartridge filters, sand filters, belt filters and plate and frame filters. Cyclone separators are not applicable to systems where the difference in the densities of the two phases is small, the shear of particles is a concern or the particles themselves are very fine. Centrifuges are very effective in solid-liquid separation however they are cost prohibitive and have the added concerns of high maintenance and excessive wear and tear on critical precision machined parts. Filter media based devices are excellent for solid-liquid separations, however they can be very prone to plugging and maintenance intensive in high solids applications. While some of these media based filtration devices are designed to self clean such as moving bed sand filters, plate and frame presses, and belt filters they require a large volume of waste water and the separation process is time consuming. The lengthy time required is not practical since the waste water changes quickly in many industrial applications and the dosage optimization system must be able to rapidly respond to the changes.

Another difficulty encountered with the fluorescent tracer technique is the introduction of air into the sample filtrate during the sampling, processing and filtering steps. Even the presence of very small air bubbles present in the filtered sample tend to cause erratic distortion in the fluorescence analysis and as a result in order to obtain reliable results the air must be removed from the sample stream prior to the sample analysis.

Tracer techniques have been used in other applications for monitoring the concentration and performance water treatment agents, for example in cooling water and boiler applications as referenced in Hoots et. al U.S. Pat. No. 4,783,314 and Hoots U.S. Pat. No. 5,171,450. These techniques are based upon set point dosage control in which a predetermined target or fixed chemical dosage for optimum treatment agent performance has been identified. The tracer is incorporated in the chemical treatment agent to maintain a set and specific dosage of a chemical treatment agent concentration in a relatively stable system where small changes in tracer concentration occur over long time periods. In these systems the interaction between the solids, which are present at very low concentrations of less than 0.1% by weight, and the liquid are not a factor in the optimization of the chemical treatment agent. The technique is not applicable in waste water treatment dosage optimization applications since partitioning of the chemical treating agent between the solid and liquid phases occurs. In waste treatment applications the primary goal is the separation of the solids from the liquids where the solids in the waste stream are typically in the range of 0.5% to 10% by weight. The optimum chemical treatment agent dosage in waste treatment applications is a moving target, not a predetermined set point and constantly varies due to erratic changes in the composition of the waste water being treated.

The primary objective of the present invention is to develop a dosage optimization system which can provide for the processing of a waste water stream to allow continuous on-stream monitoring of the performance and optimization of a chemical treating agent.

SUMMARY OF THE INVENTION

The invention comprises an apparatus for optimizing the dosage of a chemical waste water treatment agent using a fluorescent tracer by processing a sample of the waste water stream and allowing continuous on-stream monitoring of the performance of the chemical waste water treatment agent. The apparatus is comprised of a series of components that sample the waste stream, process the sample for analysis, analyze the sample, record the data in a historical database and, based upon the analysis as compared to historical data, adjust the chemical feed system to optimize the chemical waste water treatment agent according to the programmed optimization logic.

BRIEF DESCRIPTION OF THE DRAWINGS

FIG. 10 is a graph demonstrating the shift in optimum treatment chemical dosage as a result of changes in the waste water dosage requirement in a color removal application.

DESCRIPTION OF THE PREFERRED EMBODIMENT

Figure 1:
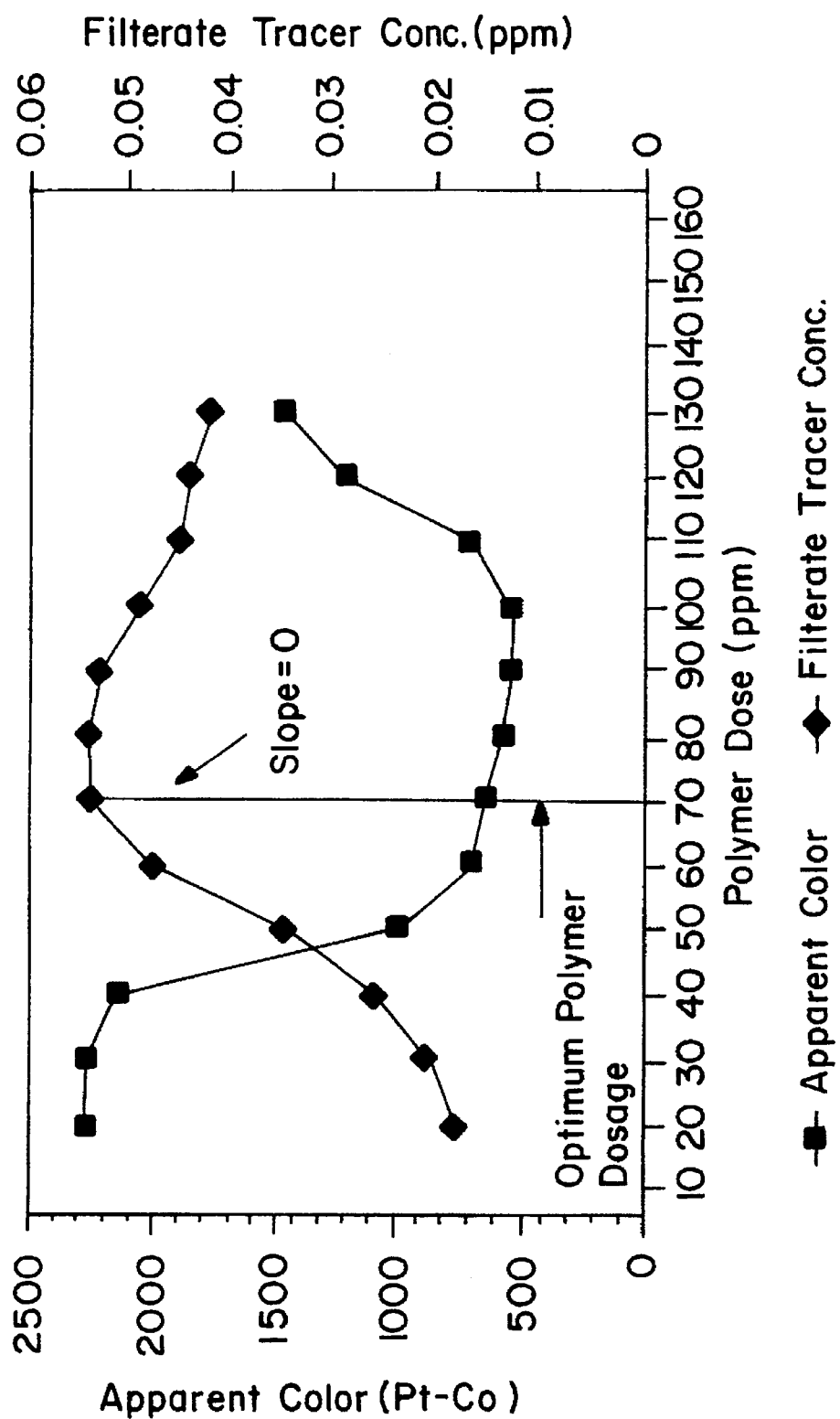
FIG. 1 is a graph comparing polymer dose to apparent color as a function of filtrate concentration for color removal.
Figure 2:
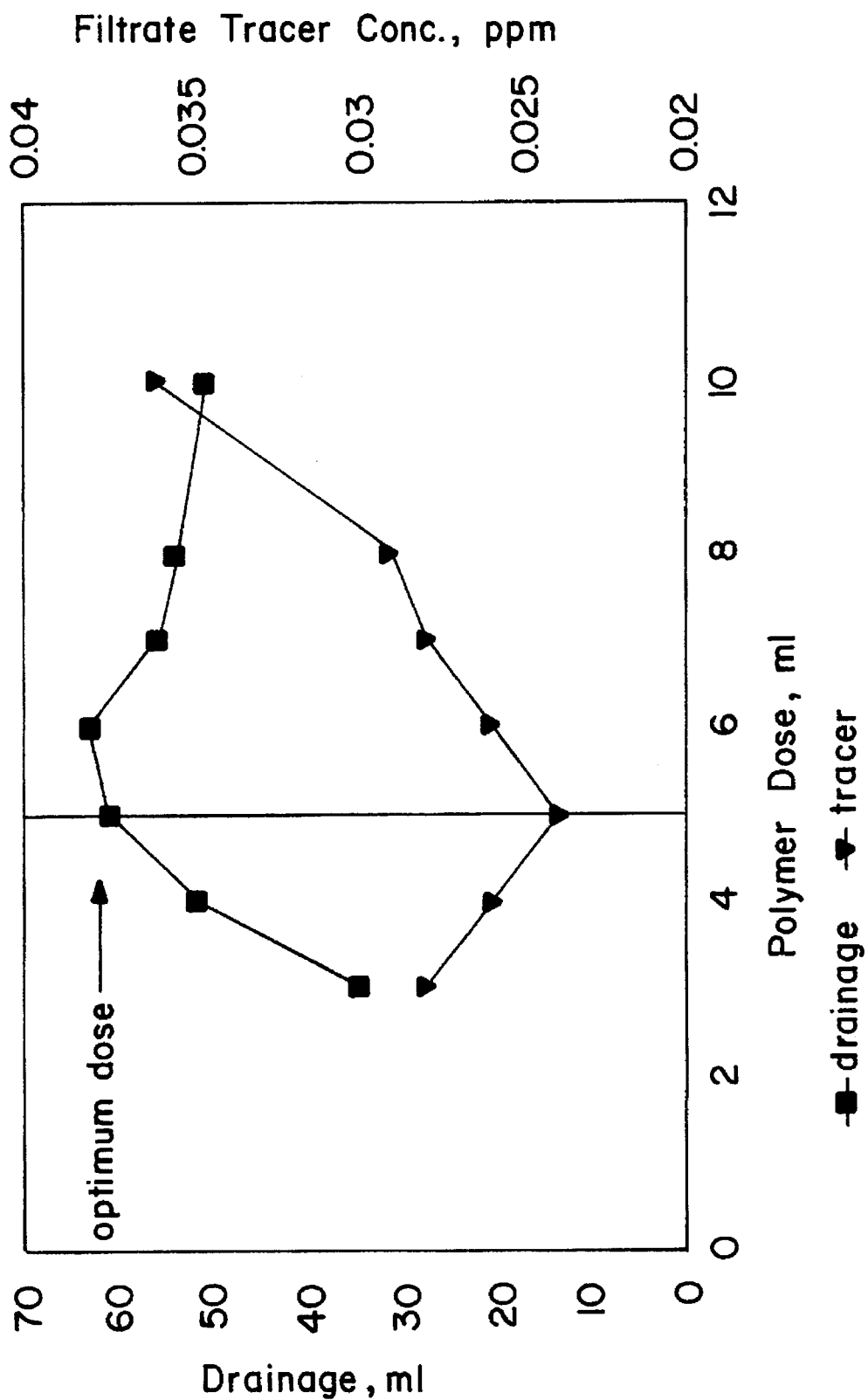
FIG. 2 is a graph comparing polymer dose to apparent color as a function of filtrate tracer concentration for sludge dewatering.

Industrial waste water systems contain solids(oils) and liquids and are often once-through systems where the waste water is not recirculated. When chemical treatment agents are used to treat the waste waters, the treatment agent partitions between the solid and liquid phases. Measurement of the chemical concentration in the water phase will indicate the dose of the optimum performance of the chemical treatment agent (FIG. 1 and FIG. 2). When a fluorescent tracer is used, the tracer will interact with the chemical treating agent and partition with the chemical between the solid and liquid phases. At this point, the residual tracer concentration in the water will be an indicator of the treatment agent performance and degree of treatment chemical optimization.

The performance of a tracer in monitoring and optimizing the chemical treatment agent performance in two wastewater treatment applications, color removal and sludge dewatering, are shown in FIGS. 1 and 2. In both cases, the breakpoint in the residual tracer concentration curve coincides with the treatment agent dose for optimum performance. The treatment agent dosage can be optimized based upon the breakpoint observed in the residual tracer concentration in the wastewater stream as described in U.S. Ser. No. 08/182,927, the disclosure of which is incorporated herein by reference.

Figure 3:
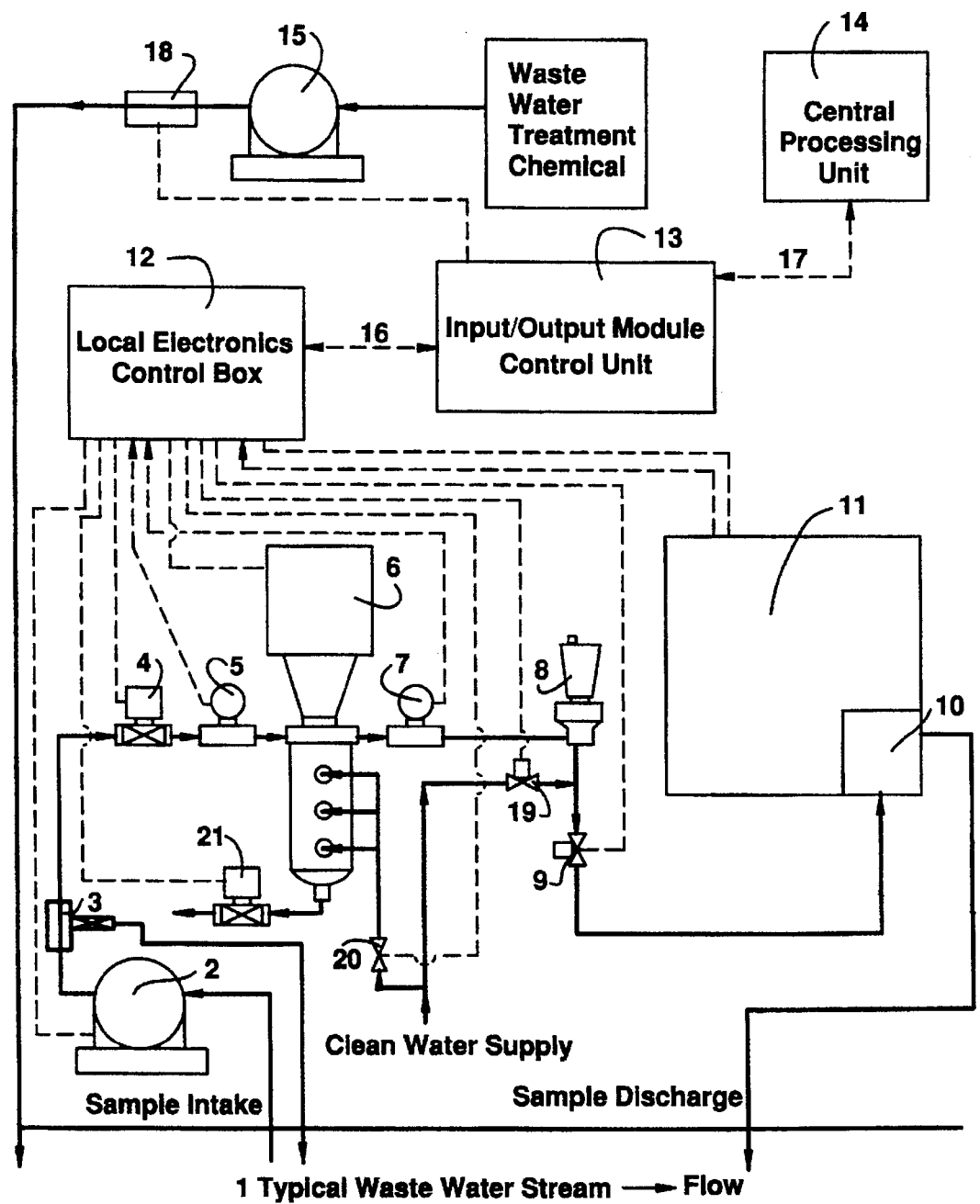
FIG. 3 is a schematic drawing showing the apparatus of the invention.

A schematic of the waste water treatment agent dosage optimization system 1, is shown in FIG. 3. Waste water is fed into the optimization system 1 by a sampling pump 2, through a pressure relief valve 3, through a rotating ball valve 4, to a transducer 5, through a filtration apparatus 6, to a transducer 7, to an air purge valve 8, through a solenoid valve 9, to the flow cell 10, of the fluorometer 11. The flow cell 10 measures colorimetric changes in the waste water filtrate and supplies a signal to the computer based software driven feedback controller 14 and the waste water is discharged. The fluorescence signal is transmitted to the local electronics box 12 and then to the data acquisition and control unit 13 through a 25 conductor communication cable 16. The data acquisition and control unit 13 then transmits a signal to the computer based software driven feedback controller 14 through a 9 conductor cable 17 where the data is stored, processed and interpreted. The controller 14 maintaines a historical record of the previous analysis performed by the apparatus. It is this historical period that is compared to the fluorometer 11 signal. Based upon the calculated slope changes in the fluorometer 11 signal the software driven feedback controller 14 then changes the treatment agent pump 15 setting by sending a new pump setting signal in communication cable 16 from the data acquisition and control unit 13.

The computer-based, software-driven feedback controller 14 controls the operation and data acquisition and historical data base of each individual component in the treatment chemical optimization system. The controller 14 controls filter cleaning cycles, and generates a record of the tracer concentration, treatment chemical feed rate and other relevant parameters as a function of time.

The input/output module control unit 13 consists of eight digital input/output modules and eight analog input/output modules and serves to interface the controller and the signals generated by or to the individual mechanical components of the system.

The waste water sampling pump 2 is preferably a positive displacement peristaltic pump. Alternatively, the pump 2 is positive displacement pump capable of producing continuous flow with low shear. The filtration apparatus 6, is preferably a Spin-Clean filter modified to allow back washing and spray washing of the chosen filter media. The Spin-Clean filter is commercially available without backwash and spray wash modifications from FiHration Specialties, Inc. Orland, Pa.

Figure 4:
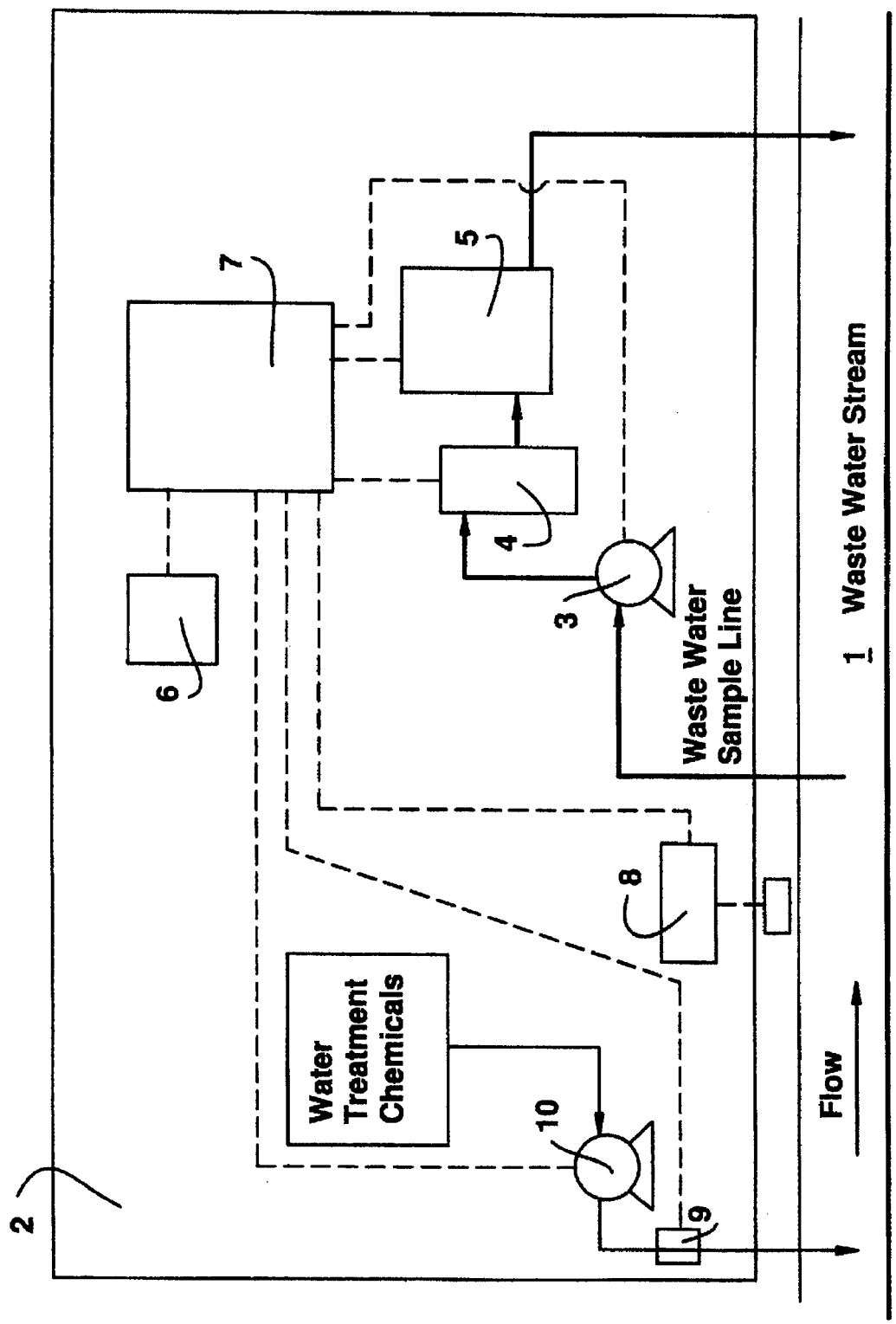
FIG. 4 is a schematic drawing showing a typical installation of the dosage optimization system in a paper mill color removal application.

FIG. 4 shows a simplified schematic of a typical installation of the polymer dosage optimization system in a paper mill color removal application. A sample of the waste water stream 1 is drawn by the sampling pump 3 of the polymer dosage optimization system 2 and pumped through the filtration apparatus 4 to the waste water analyzer 5 and then discharged back into the waste stream 1. The computer-based, software-driven feedback controller 6 communicates with the input/output module box 7 to monitor and interpret the signal from the waste water analyzer 5, the waste water flowmeter 8 and polymer feed rate flowmeter 9. Based on a series of calculations carried out by the control logic programmed into the controller 6 it will either increase or decrease the chemical treatment agent pump 10 feed rate to optimize the treatment chemical concentration in the waste water stream 1.

Figure 5:
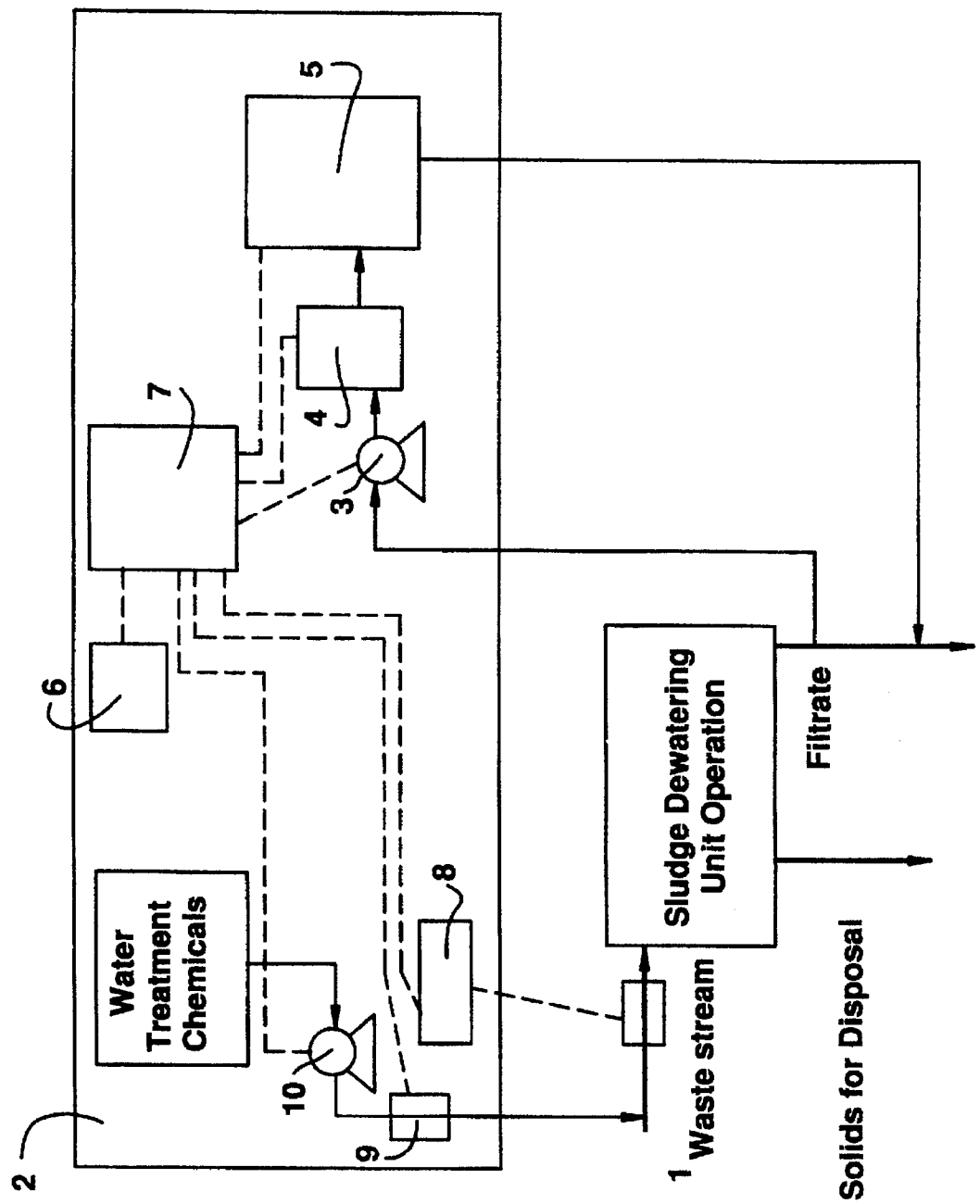
FIG. 5 is a schematic drawing showing a typical installation of the dosage optimization system in a sludge dewatering application where the sludge dewatering unit operation filtrate is analyzed.

FIG. 5 shows a simplified schematic of a typical installation of the polymer dosage optimization system in a sludge dewatering application. A sludge dewatering unit sample 1 is drawn by the sampling pump 3 of the polymer dosage optimization system 2 and pumped through the filtration apparatus 4 to the waste water analyzer 5 and then discharged back into the waste stream 1. The computer based software driven feedback controller 6 communicates with the input/output module box 7 to monitor and interpret the signal from the waste water analyzer 5, the waste water flowmeter 8 and the polymer feed rate flowmeter 9. Based on a series of calculations carried out by the control logic programmed into the controller 6 it will either increase or decrease the chemical treatment agent pump 10 feed rate to optimize the treatment chemical concentration in the waste water stream 1.

Figure 6:
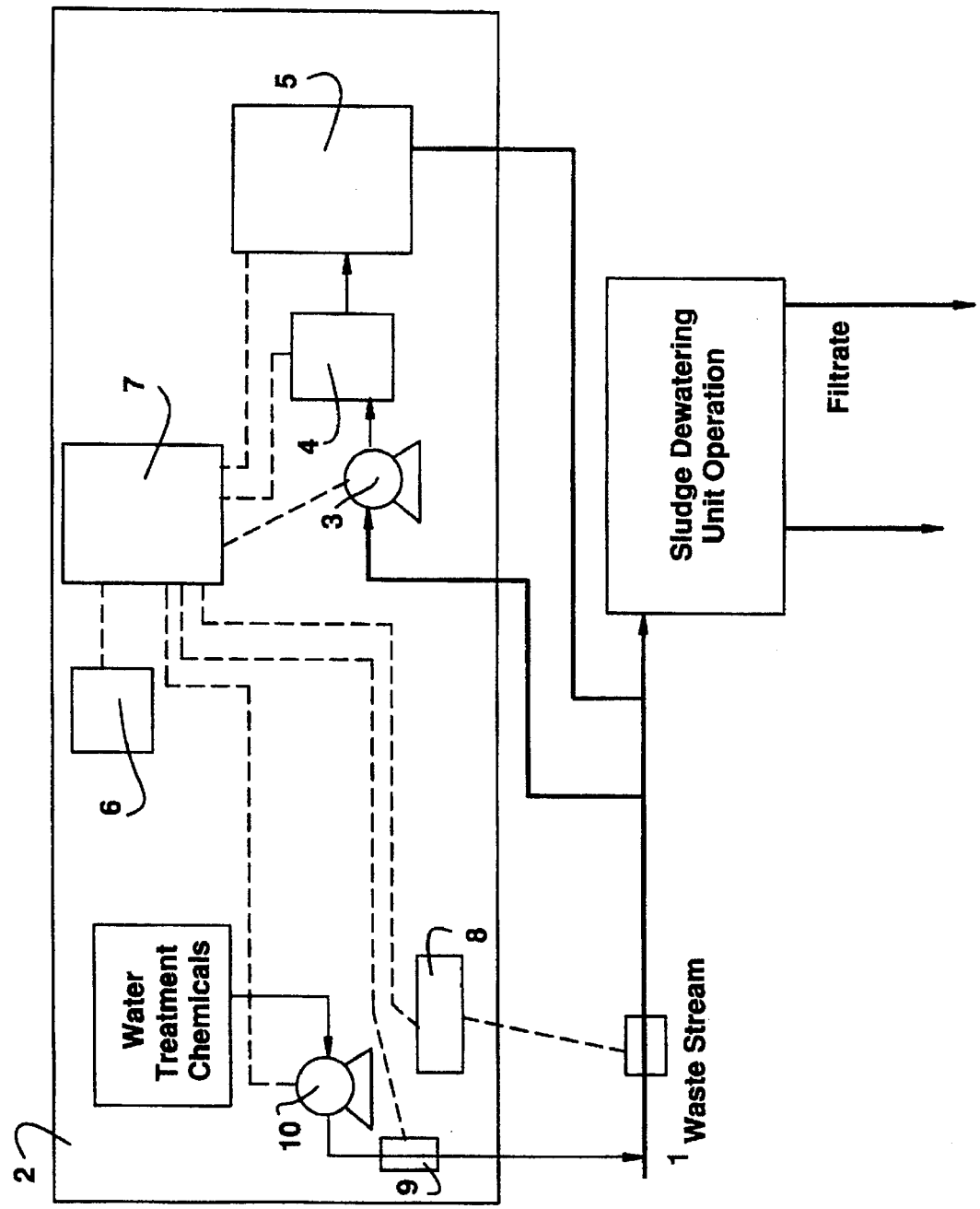
FIG. 6 shows a simplified schematic of a typical installation of the treatment agent optimization system in a second sludge dewatering application where the waste water stream to the sludge dewatering unit operation is analyzed.

FIG. 6 shows a simplified schematic of a typical installation of the polymer dosage optimization system in a slightly different sludge dewatering application. A sample of the solids-laden waste water stream 1 is drawn by the sampling pump 3 of the polymer dosage optimization system 2 and pumped through the filtration apparatus 4 to the waste water analyzer 5 and then discharged back into the waste stream 1. The computer-based, software-driven feedback controller 6 communicates with the input/output module box 7 to monitor and interpret the signal from the waste water analyzer 5, the waste water flowmeter 8 and the polymer feed rate flowmeter 9. Based on a series of calculations carried out by the control logic programmed into the controller 6 it will either increase or decrease the chemical treatment agent pump 10 feed rate to optimize the treatment chemical concentration in the waste water stream 1.

Figure 7:
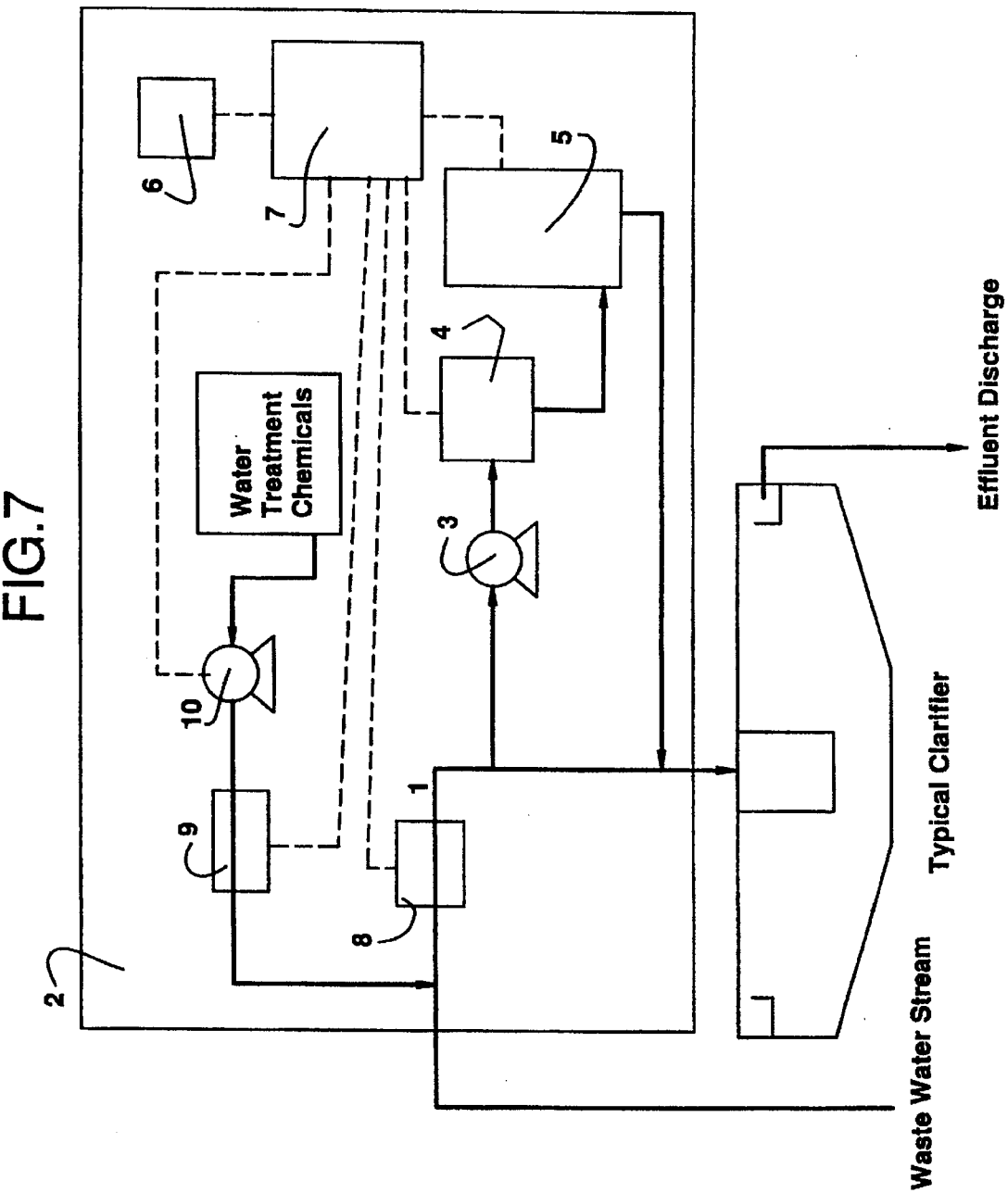
FIG. 7 is a schematic drawing showing the installation of the dosage optimization system in a typical waste water clarification application.

FIG. 7 shows a simplified schematic of a typical installation of the polymer dosage optimization system in a waste water clarification application. A sample of the solids laden waste water influent entering the clarifier 1 is drawn by the sampling 3 of the polymer dosage optimization system 2 and pumped through the filtration apparatus 4 to the waste water analyzer 5 and then discharged back into the waste stream 1. The computer-based, software-driven feedback controller 6 communicates with the input/output module box 7 to monitor and interpret the signal from the waste water analyzer 5, the waste water flowmeter 8 and the polymer feed rate flowmeter 9. Based on a series of calculations carried out by the control logic programmed into the controller 6 it will either increase or decrease the chemical treatment agent pump 10 feed rate to optimize the treatment chemical concentration in the waste water stream 1.

Figure 8:
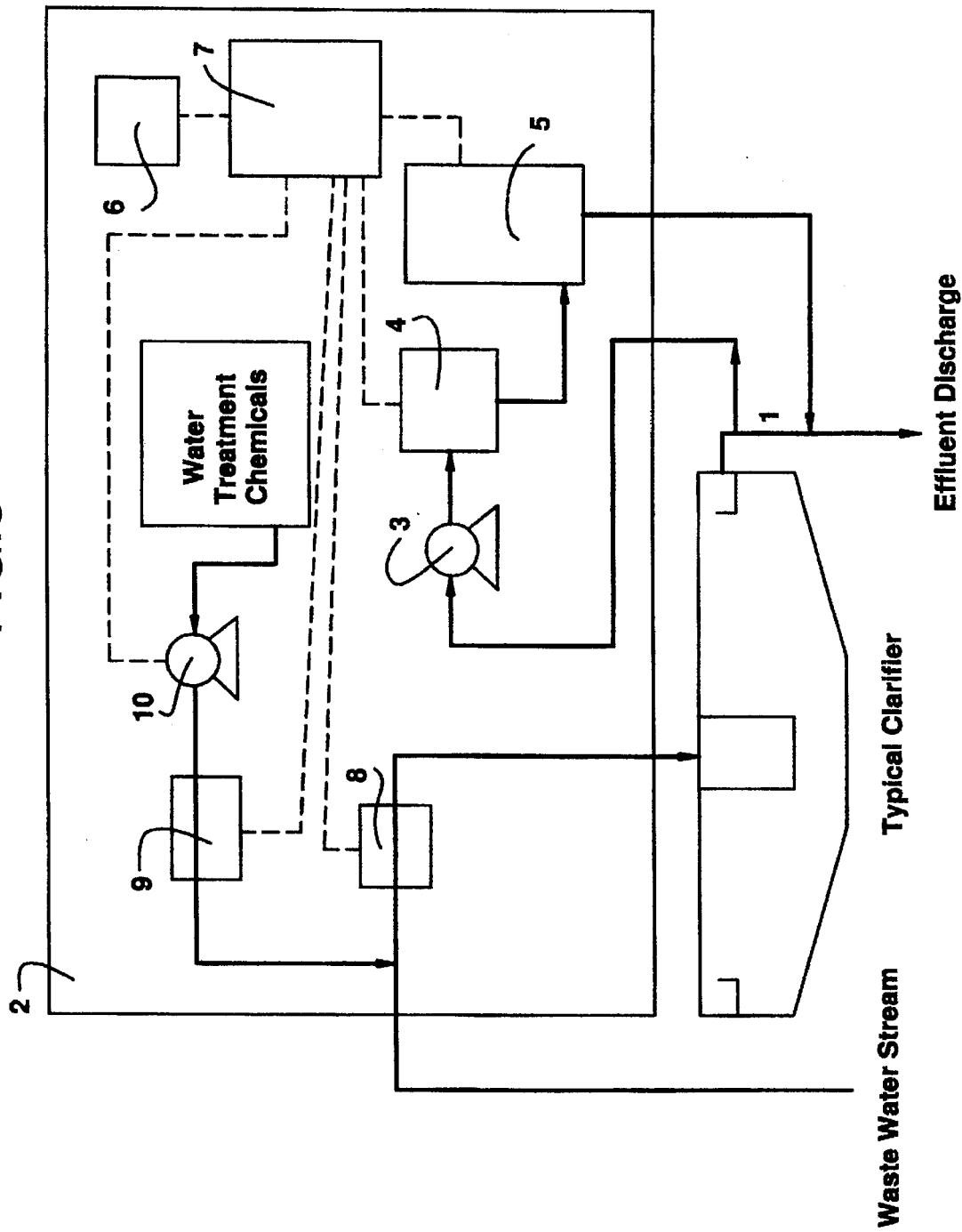
FIG. 8 is a schematic drawing showing the installation of the dosage optimization system in a second waste water clarification application.

FIG. 8 shows a simplified schematic of a typical installation of the polymer dosage optimization system in a second waste water clarification application. A sample of the waste water effluent exiting the clarifier 1 is drawn by the sampling pump 3 of the polymer dosage optimization system 2 and pumped through the filtration apparatus 4 to the waste water analyzer 5 and then discharged back into the waste stream 1. The computer-based, software-driven feedback controller 6 communicates with the input/output module box 7 to monitor and interpret the signal from the waste water analyzer 5, the waste water flowmeter 8 and the polymer feed rate flowmeter 9. Based on a series of calculations carried out by the control logic programmed into the controller 6 it will either increase or decrease the chemical treatment agent pump 10 feed rate to optimize the treatment chemical concentration in the waste water stream 1.

The change in traced waste treatment agent concentration is calculated as slope using the following equation:

$$\text{Slope} = \frac{[\text{Tracer Concentration New} - \text{Tracer Concentration Old}]}{[\text{Treatment Agent Dose New} - \text{Treatment Agent Dose Old}] + [\text{Constant}]}$$

The frequency with which the slope is calculated and compared to the target can be varied by modifying the control logic. Depending on the calculated slope, the proportional adjustment in the chemical treatment agent feedrate may be either small or large.

During a typical cleaning cycle of the treatment agent dosage optimization apparatus FIG. 3 the controller 14 will initiate cleaning cycles based upon a comparison of the monitoring of transducers 5 and 7 while continually optimizing the treatment chemical dosage. When the logic in the controller indicates that the desired condition has been met, the controller 14 will initiate a cleaning cycle. During the cleaning cycle the valve 9 is closed to eliminate flow to the analyzer 10 and valve 4 is closed to redirect the waste water stream flow. The discharge valve 21 is opened and the back flush water valve 19 and spray nozzle valve 20 are opened to clean the media and the media in 6 is spun to dislodge particulate which are then discharged to the waste stream through discharge valve 21. Each function of the cycle is independently controlled by the controller 14 and can be modified or adjusted by changes in the programmed cleaning cycle logic.

In an alternative embodiment of the apparatus in FIG. 3, the controller 14 may be programmed to initiate and carry out cleaning cycles of the filter 6 media at prescribed time intervals while continually optimizing the chemical treatment agent dosage.

The following examples are presented to describe preferred embodiments and utilities of the invention and are not meant to limit the invention unless otherwise stated in the claims appended hereto.

EXAMPLE 1

Figure 9:
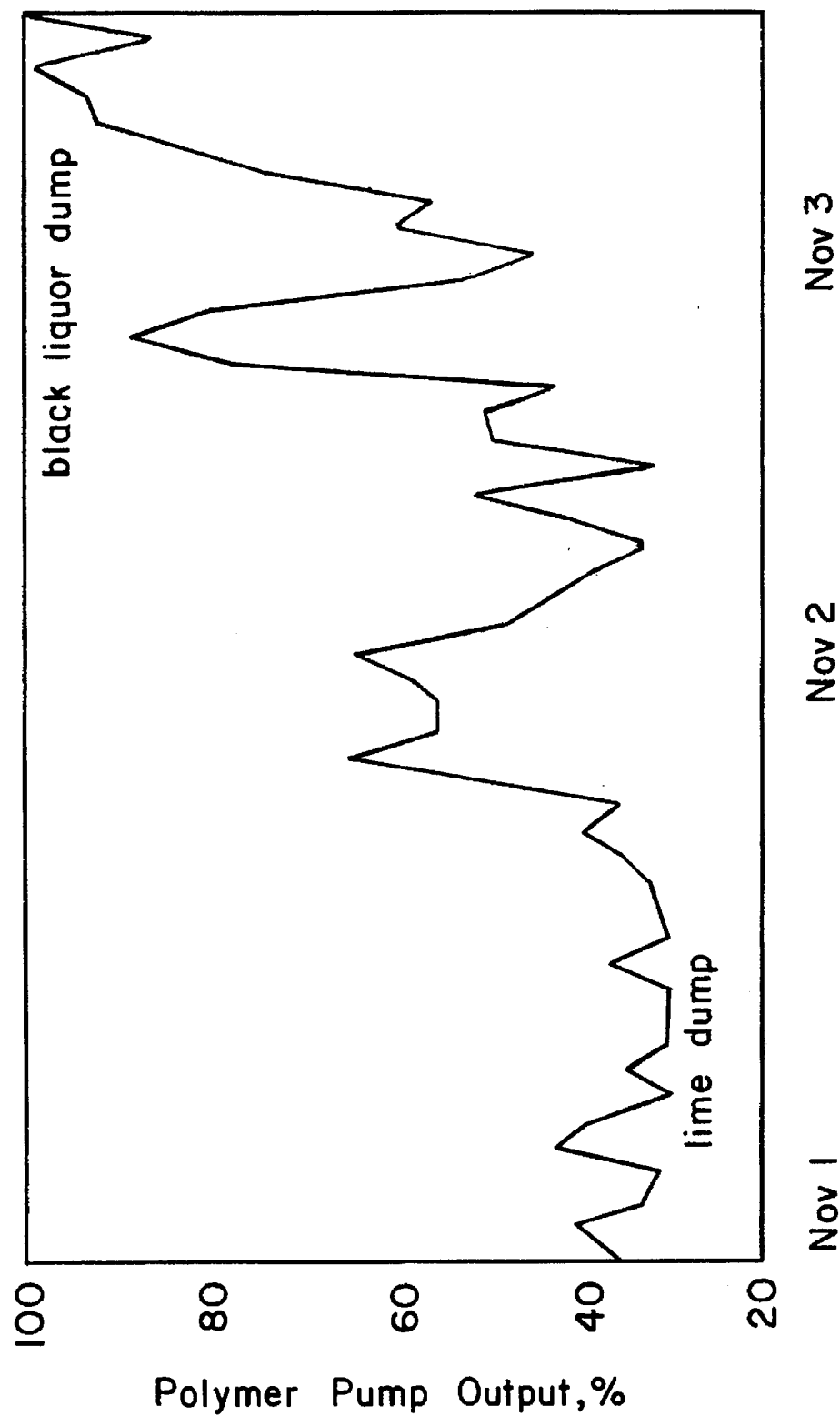
FIG. 9 is a graph comparing polymer pump output as a function of time utilizing the claimed apparatus of the invention.

A paper mill uses a waste treatment chemical agent, epi-DMA polymer to remove color from the effluent wastewater (FIG. 4). Typically the apparent color prior to treatment is about 3000 Pt-Co units. As the dosage of epi-DMA polymer is increased, the apparent color of the waste water decreases to a minimum. If the waste treatment chemical dosage is increased beyond the point where the minimum apparent color was observed the apparent color will again begin to increase steadily. In a typical industrial application the wastewater treatment agent is fed at a fixed feed rate that can be either more or less than the optimum dosage. As the wastewater composition changes due to frequent plant operational changes the optimum chemical dosage also changes (FIG. 10). With the use of the optimization apparatus and the interactive tracer, the chemical treatment agent dosage is maintained at or near the optimum dosage (FIG. 9). When the plant experiences a black liquor dump into the wastewater, the product demand increases and the dosage is automatically adjusted based upon the new demand.

EXAMPLE 2

A recycle paper mill uses a waste treatment chemical agent to facilitate in the separation of the solids and liquids in a waste stream to a sludge dewatering unit operation. In this particular case the unit operation for sludge dewatering is a twin belt press. Typically the solids in the waste water stream to the twin belt press vary in the range of 5% to 7% by weight. As the dosage of the waste treatment chemical agent is increased to the waste stream the solids content or % solids of the dewatered sludge off the press increases to a maximum. If the waste treatment chemical dosage was increased beyond the point where the maximum solids were observed the solids content would begin to decrease steadily. In a typical industrial application the wastewater treatment agent is fed at an operator selected fixed feed rate that is adjusted once an 8 hour shift, and as a result the set point dosage can be either more or less than the optimum dosage. The incoming wastewater composition changes due to frequent plant operational changes and as a result the optimum chemical dosage also changes. With the use of the optimization apparatus and the interactive tracer, the chemical treatment agent dosage is maintained at or near the optimum dosage. When the plant experiences an incoming waste water variation the product demand changes and the dosage is automatically adjusted based upon the new demand.

Changes can be made in the composition, operation and arrangement of the method of the present invention described herein without departing from the concept and scope of the invention as defined in the following claims:

We claim:

1. An apparatus for optimizing the dosage of a chemical waste water treatment agent to a waste water treatment system, comprising:

a metering pump attached to the waste water treatment system, the pump being constructed and adapted to pump water having a substantial solids content, the pump being capable of accepting an external pump control signal for providing an amount of fluorescently traced chemical treatment agent to the waste water treatment system;

an extraction pump located down stream from the metering pump to continuously extract a representative sample of waste water treated with a traced chemical treatment agent from the waste water treatment system, the sample comprising a water phase filtrate and a solid phase;

a filtration apparatus connected to the extraction pump for continuously separating the chemical treatment agent by separating suspended solids from the filtrate;

an air removal unit connected to the titration apparatus to continuously remove air entrained in the sample during sampling, processing and separation of the wastewater sample;

an analyzer connected to the air removal unit for analyzing the filtrate of the extracted waste water, wherein the analyzer is selected from the group consisting of a fluorometer, a streaming current detector and a colorimeter and wherein the analyzer is in electronic communication with a recorder that maintains records of the analysis carried out by the analyzer;

an electronic storage component that is in electronic communication with the recorder, the storage component comprising a database containing historical records of previous analysis of samples taken from the system; and an optimization controller that is in electronic communication with the metering pump and the recorder and which contains the storage component, wherein the controller optimizes the chemical treatment agent dosage by comparing the analysis records in the recorder to the historical records in the electronic storage component and signalling the metering pump to adjust the amount of chemical waste water treatment agent according to optimal standards obtained from the historical records.

2. An apparatus according to claim 1, wherein the air removal unit is selected from the group consisting of air traps and air purges.

3. An apparatus according to claim 1, wherein the extraction pump is selected from the group consisting of a peristaltic pump, a diaphragm pump and a positive displacement pump.

4. An apparatus according to claim 1, wherein the filtration apparatus is capable of accommodating filtration media having typical pore sizes of from about 10 microns to about 200 microns.

5. An apparatus according to claim 1, wherein the controller is a computer.

6. An apparatus according to claim 1, wherein the metering pump provides traced chemical treatment agent by adjusting the pump speed dependent on the signal from the controller.

7. An apparatus according to claim 1, wherein the controller monitors the condition of the filtration apparatus.

8. An apparatus according to claim 1, wherein the controller initiates cleaning of the filtration apparatus, the cleaning being initiated when the condition of the filtration apparatus is less than preprogrammed parameters in the controller.

* * * * *

UNITED STATES PATENT AND TRADEMARK OFFICE
CERTIFICATE OF CORRECTION

PATENT NO. : 5,645,799
DATED : July 8, 1997
INVENTOR(S) : Jitendra T. Shah, et al.

It is certified that error appears in the above-indentified patent and that said Letters Patent is hereby corrected as shown below:

Column 8, line 9, claim 1, an air removal unit connected to the titration apparatus to...

SHOULD READ AS:

an air removal unit connected to the filtration apparatus to...

Signed and Sealed this

Seventh Day of October, 1997

*Attest:*

BRUCE LEHMAN

*Attesting Officer*     Commissioner of Patents and Trademarks